US005384243A

United States Patent [19]

Gutkind et al.

[11] Patent Number: 5,384,243

[45] Date of Patent: Jan. 24, 1995

[54] METHOD FOR SCREENING AN AGENT FOR ITS ABILITY TO PREVENT CELL TRANSFORMATION

[75] Inventors: J. Silvio Gutkind, Silver Spring, Md.; Keith C. Robbins, Reston, Va.

[73] Assignee: The United States of America as represented by the Department of Health and Human Services, Washington, D.C.

[21] Appl. No.: 989,981

[22] Filed: Dec. 11, 1992

Related U.S. Application Data

[63] Continuation of Ser. No. 683,967, Apr. 12, 1991, abandoned.

[51] Int. Cl.[6] .................... C12N 5/00; C12N 15/00; C12Q 1/24; C12Q 1/04

[52] U.S. Cl. .................... 435/6; 435/240.1; 435/240.2; 435/172.1; 435/172.3; 435/320.1; 435/30; 435/34

[58] Field of Search .................... 435/240.1, 240.2, 172.1, 435/320.1, 172.3, 2, 4, 5, 6, 30, 31, 32, 34; 574/26, 28; 564/345; 548/429

[56] References Cited

U.S. PATENT DOCUMENTS 4,937,232 6/1990 Bell et al. .................... 514/26

OTHER PUBLICATIONS

J. Downward, et al., "Close Similarity of Epidermal Growth Factor Receptor and v-erb-B Oncogene Protein Sequences", Nature, vol. 307, Feb. 9, 1984, pp. 521-527.

Fernando Leal, et al., "Evidence That the v-sis Gene Product Transforms by Interaction with the Receptor for Platelet-Derived Growth Factor", Science, vol. 230, Oct. 18. 1985, pp. 327-330.

Tai Kubo, et al., "Cloning, Sequencing and Expression of Complementary DNA Encoding the Muscarinic Acetylcholine Receptor", Nature, Oct. 2, 1986, pp. 411-416.

Dallan Young, et al., "Isolation and Characterization of a New Cellular Oncogene Encoding a Protein with Multiple Potential Transmembrane Domains", Cell, vol. 45, Jun. 6, 1986, pp. 711-719.

Yarden, et al., "Structure of the Receptor for Platelet-Derived Growth Factor Helps Define a Family of Closely Related Growth Factor Receptors", Nature, vol. 323, Sep. 18, 1986, pp. 226-232.

Thierry J. Velu, et al., "Epidermal Growth Factor-Dependent Transformation by a Human EGF Receptor Proto-Oncogene", Science, vol. 238, May 29, 1987, pp. 1408-1410.

Pier Paolo Di Fiore, et al., "Overexpression of the Human EGF Receptor Confers an EGF-Dependent Transformed Phenotype to NIH 3T3 Cells", Cell, vol. 51, Dec. 24, 1987, pp. 1063-1070.

Ernest G. Peralta, et al., "Distinct Primary Structures, Ligand-Binding Properties and Tissue-Specific Expression of Four Human Muscarinic Acetylcholine Receptors", The EMBO Journal vol. 6, Nov. 13, 1987, pp. 3923-3929.

T. I. Bonner, et al., "Identification of a Family of Muscarinic Acetylcholine Receptor Genes", Science, vol. 237, Jul. 31, 1987, pp. 527-532.

Bruce R. Conklin, et al., "Stimulation of Arachidonic Acid Release and Inhibition of Mitogenesis by Cloned Genes for Muscarinic Receptor Subtypes Stably Expresses in A9 L Cells", Proc. Natl. Acad. Sci., vol. 85, Nov. 1988, pp. 8698-8702.

(List continued on next page.)

*Primary Examiner*—Robert J. Hill, Jr.
*Assistant Examiner*—Gian P. Wang
*Attorney, Agent, or Firm*—Knobbe, Martens, Olson & Bear

[57] ABSTRACT

The present invention relates, in general, to a method of screening agents. In particular, the present invention relates to a method of testing the cancer preventing activity of a drug and of testing an agent for its ability to prevent cell transformation.

9 Claims, 6 Drawing Sheets

OTHER PUBLICATIONS

Toshimitus matsui, et al., "Isolation of a Novel Receptor CDNA Establishes the Existance of Two PDGF Receptor Genes", Science, vol. 243, Feb. 10, 1989, pp. 800–804.

S. V. Penelope Jones, et al., "Cloned Muscarinic Receptor Subtypes Expressed in A9 Cells Differ in Their Coupling to Electrical Responses", Molecular Pharmacology, vol. 34, Jul. 11, 1988, pp. 421–426.

Tom I. Bonner, "m5 Muscarinic Acetylcholine Receptor Genes" Neuron, vol. 1, 1988, pp. 403–410.

Ernest G. Peralta, et al. "Differential Regulation of PI Hydrolysis and Adenylyl Cyclase by Muscarinic Receptor Subtypes", Nature, vol. 334, Aug. 4, 1988, pp. 434–436.

Fukuda, et al., "Selective Coupling with K+ Currents of Muscarinic Acetylcholine Receptor Subtypes in NG108-15 Cells", Nature, vol. 335, Sep. 22, 1988, pp. 355-358.

David Julius, et al., "Ectopic Expression of the Serotonin lc Receptor and the Triggering of Malignant Transformation", Science, vol. 244, Jun. 2, 1989, pp. 1057-1062.

Avi Ashkensazi, et al., "Acetylcholine Analogue Stimulates DNA Synthesis in Brain-Derived Cells Via Specific Muscarinic Receptor Subtypes", Nature, vol. 340, Jul. 31, 1989, pp. 146–150.

Angela K. Thompson, et al. "Relationship Between Agonist-Induced Muscarinic Receptor Loss and Desensitization of Stimulated Phophoinositide Turnover in Two Neuroblastomas: Methodological Considerations", The Journal of Pharmacology and Experimental Therapeutics, vol. 252, Oct. 30, 1990, pp. 744–752.

J. Trejo et al., "Muscarinic Receptor Stimulation Induces C-FOS Through a PKC Dependent Mechanism in 1321N1 But Not in NG108-15 Cells", The FASEB Journal, vol. 4, No. 7, Apr. 1990.

J. Silvio Gutkind, et al., "Muscarinic Acetylcholine Receptor Subtypes as Agonist-Dependent Oncogenes", Proc. Natl. Acad. Sci. USA, vol. 88, Jun. 1991, pp. 4703–4707.

Trejo et al. (Jun. 4–7, 1990), The FASEB Journal, vol. 4, No. 7: A2097, #2386.

Thompson et al. (Feb., 1990), The Journal of Pharmacology and Experimental Therapeutics, vol. 252, #2, pp. 744–752.

Fig.3 A
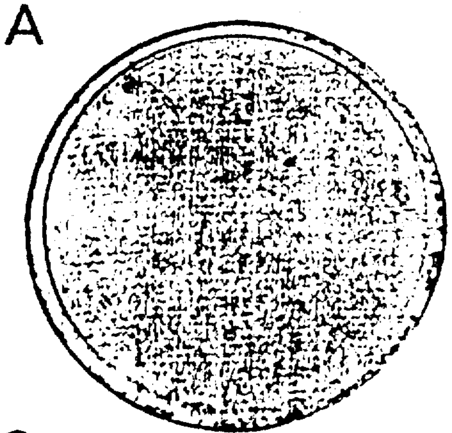
Fig.3 C
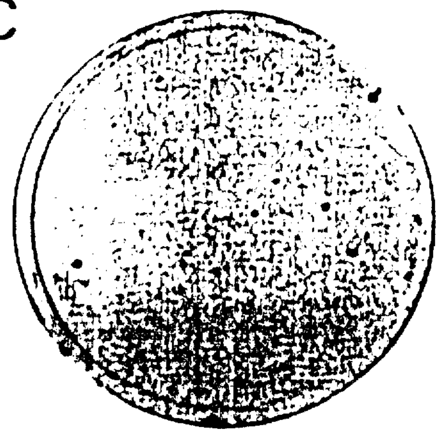
Fig.3 E

METHOD FOR SCREENING AN AGENT FOR ITS ABILITY TO PREVENT CELL TRANSFORMATION

This application is a continuation of application Ser. No. 07/683,967, filed Apr. 12, 1991, now abandoned.

BACKGROUND OF THE INVENTION

Field of the Invention

The present invention relates, in general, to a method of screening drugs. In particular, the present invention relates to a method of reversibly transforming cells and to a method of screening agents for their ability to prevent cell transformation.

Background Information

Receptors for polypeptides such as epidermal growth factor and platelet-derived growth factor can induce cellular transformation when constitutively activated (DiFiore, P. P., et al. (1987) *Cell* 51, 1063–1070; Downward, J., et al. (1984) *Nature (London)* 307, 521–527; Leal, F., et al. (1985) *Science* 230, 327–330; Velu, T. J., et al. (1987) *Science* 238, 1408–1410). Structural mutations or unregulated availability of ligand are mechanisms known to account for their transforming activity. These receptors are prototypes of a class that mediate signal transduction by virtue of an intrinsic protein-tyrosine kinase (PTK) activity (Downward, J., et al. (1984) *Nature* (London) 307, 521–527;Yarden, Y., et al. (1986) *Nature* (London) 323, 226–232; Matsui, T., et al. (1989) *Science* 243, 800–804). When the mas oncogene was discovered, a class of cell-surface receptors lacking PTK domains was also implicated in cellular transformation. The mas oncogene product has a structural motif characteristic of receptors which mediate signal transduction by coupling to GTP binding proteins (G-proteins) (Young, D., et al. (1986) Cell 45, 711–719). Although mas has a weak focus-inducing activity in vitro, cells transfected with this gene are highly tumorigenic in nude mice (Young, D., et al. (1986) *Cell* 45, 711–719). More recently, G-protein coupled serotonin receptors have been shown to convert fibroblasts to a tumorigenic state (Julius, D., et al. (1989) *Science* 244, 1057–1062). Since in these latter cases exogenous ligand is not required for transformation, these genes encoding either aberrant receptors, or endogenous ligands are responsible for their activation. Thus, ligand independence has limited the study of the mechanism by which these receptors mediate transformation.

SUMMARY OF THE INVENTION

It is an object of this invention to provide a method of reversibly transforming cells.

It is another object of this invention to provide a method of testing an agent for its ability to prevent cell transformation.

Further objects and advantages of the present invention will be clear from the description that follows.

DETAILED DESCRIPTION OF THE INVENTION

Figure 1:
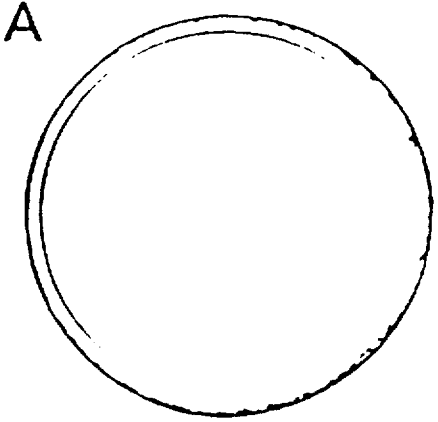
FIG. 1. Focus assay after transfection of NIH/3T3 cells with mACHR DNAs. NIH/3T3 cells were transfected with 1 μg of pDS (A), 0.3 μg of pDS v-fgr (B), or 1 μg of pDS ml (C-F) plasmid DNA. Cultures were maintained in Dulbecco's modified Eagle's medium (A-C), supplemented with 100 μM carbachol (D), 10 μM atropine (E), or 100 μM carbachol and 10 μM atropine in combination (F). Plates were stained 3 weeks after transfection.
Figure 1:
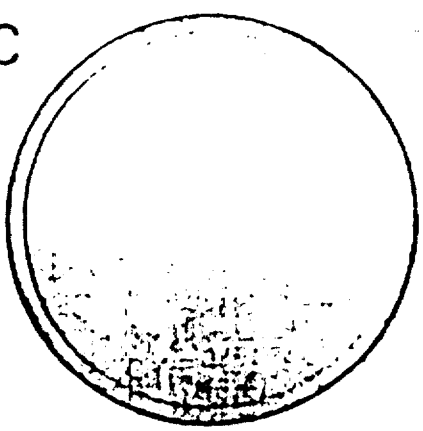
Figure 1:
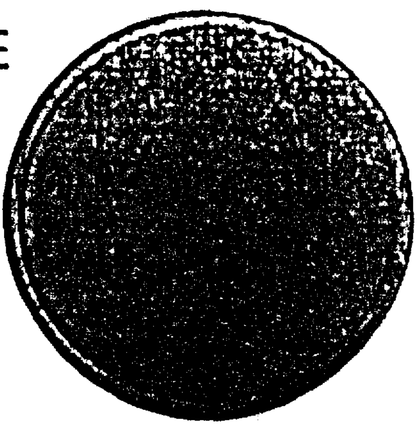
Figure 1:
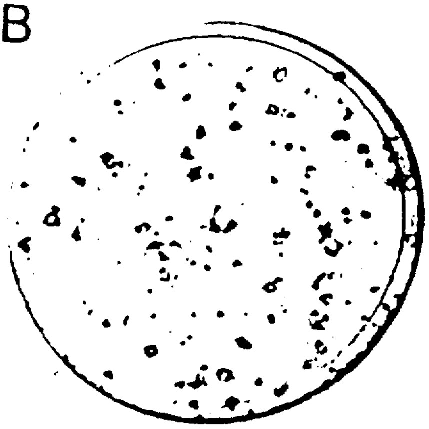
Figure 1:
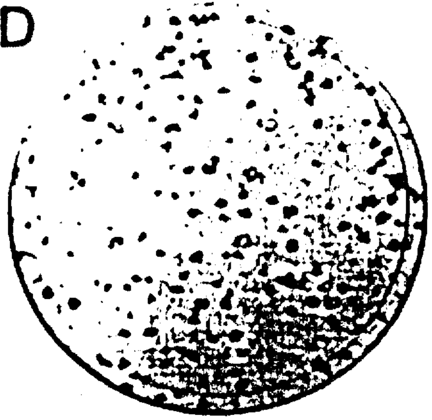
Figure 1:
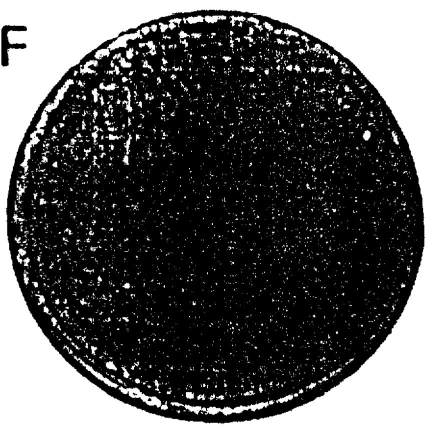

The present invention relates to a method of reversibly transforming cells and to a method of using such cells for screening agents for prophylactic efficacy.

The present invention derives from applicant's demonstration that transformed cells can be reverted to the non-transformed state. The applicant has evaluated the muscarinic acetylcholine family of G-protein coupled receptors (mACHRs) for their oncogenic potential. The family of cell surface neurotransmitter receptors, human muscarinic acetylcholine receptors (mACHRs), was chosen that possess sequence homology with both mas and the serotonin receptor (Kubo, T., et al. (1986) *Nature* (London) 323,411–416; Peralta, E. G, et al.

(1987) *EMBO J.* 6, 3923–3929; Bonner, T. I., et al. (1987) *Science* 237, 527–532; Bonner, T. I., et al. (1988) *Neuron* 1, 403–410). Muscarinic receptors are preferentially expressed in neurons and other postmitotic cells, and they transduce signals specified by their endogenous agonist, the neurotransmitter acetylcholine. The mACHR family consists of five distinct but highly homologous subtypes (m1–m5) which are encoded by five separate genes (Kubo, T., et al. (1986) *Nature* (London) 323, 411–416; Peralta, E. G., et al. (1987) *EMBO J.* 6, 3923–3929; Bonner, T. I., et al. (1987) *Science* 237, 527–532;Bonner, T. I., et al. (1988) *Neuron* 1, 403–410). Individual mACHRs have functional differences when expressed by cultured cells. Odd numbered mACHRs potently stimulate phosphatidylinositol metabolism, arachidonic acid release, and open $Ca^{2+}$-dependent potassium channels by coupling with a pertussis toxin (PTX) insensitive G-protein. m2 and m4 mACHRs couple to a PTX sensitive G-protein to inhibit adenylyl cyclase (Jones, S.V.P., et al. (1988) *Mol. Pharmacol.* 34, 421–426; Peralta, E. G., et al. (1988) *Nature* 334,434–437; Fukuda, K., et al. (1988) *Nature* 335, 355–358). Depending upon assay conditions, m1, m3 and m5 mACHRs have been linked to both increases (Ashkenazi, et al. (1989) *Nature* 340, 146–150) and decreases (Conklin, B. R. et al. (1988) *Proc. Natl. Acad. Sci. U.S.A.* 85, 8698–8702) in mitogenesis.

mACHR receptors are preferentially expressed in post-mitotic cells and transducing signals are specified by an endogenous agonist (for example acetylcholine). Cells transfected with individual human mACHR genes were morphologically indistinguishable from parental NIH/3T3 cells in the absence of agonist. In contrast, when cultures were supplemented with an agonist (for example, carbachol, a stable analog of acetylcholine), foci of transformation readily appeared in m1, m3, or m5, but not m2 or m4 mACHRs transfectants. Receptor expression was verified by ligand binding and was found to be similar for each transfected culture. Transformation was dose-dependent and required only low levels of receptor expression. In transformation competent cells, agonist induced phosphatidylinositol (PI) hydrolysis, whereas in m2 or m4 transfectants, receptors were coupled to the inhibition of adenylyl cyclase. The present invention demonstrates that genes (specifically, mACHR genes) encoding receptors linked to phosphatidylinositol hydrolysis can act as conditional oncogenes when expressed in cells capable of proliferation.

In one embodiment, the present invention relates to a method of reversibly transforming cells comprising:

(1) introducing DNA containing an expression vector carrying the gene for a G-protein-coupled receptor linked to phosphatidylinositol metabolism into a mammalian cell, (2) culturing said cell on medium containing an agonist, and (3) scoring for agonist-dependent neoplastic transformation.

In another embodiment, the present invention relates to a method of testing an agent for its ability to prevent cell transformation. The method comprises:

(1) introducing DNA containing an expression vector carrying the gene for a G-protein-coupled receptor linked to phosphatidylinositol metabolism into a mammalian cell, (2) culturing the cell on medium containing the test drug, (3) adding agonist simultaneously or at some later time, and (4) scoring for agonist-dependent neoplastic transformation.

In the present invention, it was found that normal G-protein coupled receptors can induce agonist-dependent neoplastic transformation. Other G-protein coupled receptors, such as receptors for angiotensin, serotonin, thrombin, endothelin, substance K, substance P, bradiokynin, and adrenaline are predicted to behave similarly as m1 mACHR. In the above-described methods, the receptor gene may be m1 or m3 ACHR; the DNA introduced may be pDS m1 or pDS m3. Cells useful in the above-described invention include mammalian cells (such as human or mouse cells; including NIH/3T3 cells). Introduction of the recombinant molecule into the host cell can be effected using methods known in the art. The above-described agonist may be an acetylcholine analog (for example, carbachol). Other analogs such as bethanecol, methacholine, and pilocarpine could be utilized for this assay.

The present invention is described in further detail in the following non-limiting examples.

EXAMPLES

The following protocols and experimental details are referenced in the examples that follow:

Transfection. Transfection of NIH/3T3 (Jainchill, J. L., et al. (1969) *J. Virol.* 4, 549–553) cells with plasmid DNA was performed by the calcium phosphate precipitation technique, as modified by Wigler et al. (Wigler, M., et al. (1977) *Cell* 11, 223–232). Mass populations expressing the transfected neogene were selected for their ability to grow in the presence of geneticin (G418) (Gibco). Transformed foci were scored in stained plates of NIH/3T3 2–3 weeks after transfection. Individual G418 colonies or transformed foci were isolated with the aid of cloning cylinders, and maintained in Dulbecco's Modified Eagle Medium containing 10% calf serum.

DNA Constructs. Human mACHRs genes (Bonner, T. I., et al. (1987) *Science* 237, 527–532; Bonner, T. I., et al. (1988) *Neuron* 1, 403–410) were inserted into an expression vector, pDS, which contained a dominant selectable marker, neo (Korman, A. J., et al. (1987) *Proc. Natl. Acad. Sci. U.S.A.* 84, 2150–2154). pDS v-fgr was derived from pSV2v-fgr, which contained the biologically active GR-FeSV proviral genome (Naharro, G., et al. (1983) *J. Virol.* 47, 611–619; Naharro, G., et al. (1984) *Science* 223, 63–66). *Analysis of Receptor Expression.* Cell membranes were isolated and binding assays were performed as previously described (Buckley, N. J., et al. (1989) *Mol. Pharmacol.* 35, 469–476). Saturation experiments were performed at ten different concentrations of [$^3$H]N-methylscopolamine (1 pM to 1 nM) in duplicate. Data were fit using nonlinear regression with the equation $Y=B_{max}X^N/K_d/(1-B_{max}X^N/K_d)$ with the program KALIDOGRAPH on a Mac II computer, where y is specific binding and X is free ligand concentration. Nonspecific binding was determined with 10 $\mu$M atropine.

Phosphatidylinositol Hydrolysis. Subconfluent NIH/3T3 transfectants were incubated in 24 well plates with 1 $\mu$Ci/ml [$^3$H]myo-inositol for 48 hrs. Immediately prior to an experiment, the cells were washed twice with Eagle's medium containing 10 mM LiCl and incubated for 10 min at room temperature. Cells were treated for 1 hr with 0.5 ml of medium containing 10 mM LiCl and experimental agents. Inositol phosphates were extracted with 0.5 ml of ice-cold 10% (wt/vol) trichloroacetic acid and analyzed by ion-exchange chromatography by the method of Berridge et al. (Berridege, M. J., et al. (1983) *Biochem. J.* 212, 473–482). Ten concentrations of carbachol (50 nM–333 μM) were used to determine $ED_{50}$ and maximal responses.

cAMP Assays. Transfected NIH/3T3 cells were grown to 90% confluence in 24-well plates. Medium was replaced with 0.25 ml of Eagle's medium containing 1 mM 3-isobutyl-1-methylxanthine and experimental agents. The reaction was stopped after 10 min of incubation at room temperature by adding 0.25 ml of an ice-cold solution containing 0.1N HCl and 1 mM $CaCl_2$. The medium was removed and the cAMP acetylated with 50 μl of acetic anhydride in triethanolamine buffer. cAMP levels were determined using a GAMMAFLOW automated radioimmunoassay for acetylated cAMP (Atto Instruments, Potomac, Md.) as previously described (Buckley, N. J., et al. (1989) *Mol. Pharmacol.* 35, 469–476).

EXAMPLE 1

Conditional Transformation of Certain mACHR Transfectants.

Expression plasmids carrying each of the human mACHRs were transfected into NIH/3T3 cells, a murine fibroblast lacking endogenous mACHRs (Jainchill, J. L., et al. (1969) *J. Virol.* 4, 549–553). Expression of each mACHR gene was driven by the Moloney leukemia virus long terminal repeat, a potent transcriptional promoter in NIH/3T3 cells. The same constructs also contained a dominant selectable marker, neo (Korman, A. J., et al. (1987) *Proc. Natl. Acad. Sci. U.S.A.* 84, 2150–2154) that conferred resistance to geneticin (G418), thereby permitting determination of transfection efficiencies. As shown in TABLE 1, the number of colonies resistant to the cytotoxic effect of high concentrations of G418 (neo-resistant colonies) was nearly identical for all plasmid DNAs tested except for m5 which was not further examined. In contrast, transforming activity varied widely among DNA constructs. The v-fgr oncogene (Naharro, G., et al. (1983) *J. Virol.* 47, 611–619; Naharro, G., et al. (1984) *Science* 223, 63–66) efficiently induced focus-formation, whereas mACHR transfectants appeared morphologically indistinguishable from parental NIH/3T3 or vector transfected cells (TABLE 1). However, when maintained in the presence of carbachol, a stable analog of acetylcholine, foci of transformation readily appeared in cultures transfected with m1 or m3, but not m2 or m4 mACHR genes (TABLE 1). Focus-formation increased as a function of agonist concentration (TABLE 1), and carbachol-induced transformation was prevented by the muscarinic antagonist atropine (FIG. 1).

TABLE 1

Focus-forming activity of cloned human muscarinic acetylcholine receptors.

| DNA clone | Focus-forming Activity Per pmol DNA Carbachol (M) 0 | $10^{-6}$ | $10^{-4}$ | Colony-forming Activity Per pmol DNA |
|---|---|---|---|---|
| pDS | <1 | <1 | <1 | 2,800 |
| pDS m1 | <1 | 36 | 580 | 2,400 |
| pDS m2 | <1 | <1 | <1 | 2,400 |
| pDS m3 | <1 | 34 | 280 | 1,900 |
| pDS m4 | <1 | <1 | <1 | 2,600 |
| pDS m5 | <1 | <5 | 47 | 600 |
| pDS v-fgr | 1900 | — | — | 3,700 |

Human mACHRs genes or v-fgr were inserted into an expression vector, pDS, and 0.05–1 μg of plasmid DNA was transfected into NIH/3T3 murine fibroblasts (Jainchill, J. L., et al. (1969) *J. Virol.* 4, 549–553) as previously described (Wigler, M., et al. (1977) *Cell* 11, 223–232). Media containing varying concentrations of the muscarinic cholinergic agonist, carbachol, or the muscarinic cholinergic antagonist, atropine (10 μM), was replaced every 2 days. Foci of transformation were scored after 2–3 weeks. The efficiency of transfection was determined by scoring neo resistant colonies in medium containing G418 (0.750 mg/ml). No foci of transformation were observed in cells maintained in the presence of atropine, and atropine abolished carbachol induced focus-formation (data not shown). Results represent the average of three independent experiments.

EXAMPLE 2

Agonist Requirement for Maintenance of the Transformed State

Figure 2A:
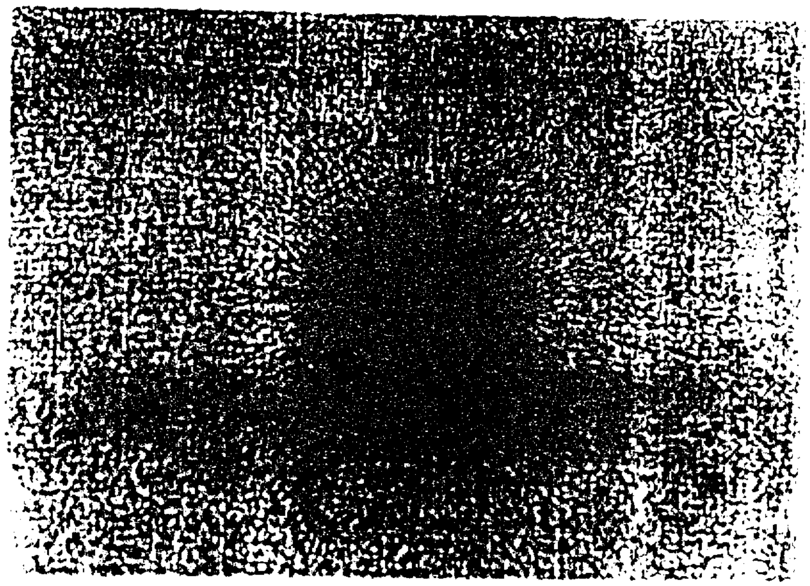
FIG. 2. Reversibility of transformation in NIH/3T3 expressing ml mACHR. A) A focus of transformation that arose 2 weeks after transfection with 1 μg of pDS ml DNA in the presence of the muscarinic cholinergic agonist carbachol. B) The focus was isolated with the aid of a cloning cylinder, trypsinized, and plated on a lawn of NIH/3T3 cells in medium lacking carbachol.
Figure 2B:
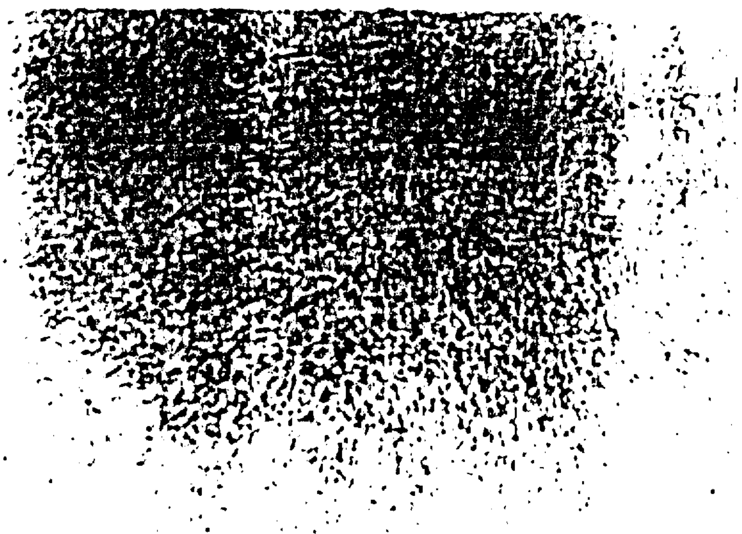

To determine whether transformation of m1 and m3 ACHR transfectants required agonist for the maintenance of their transformed state, foci were picked and replated on a lawn of untransfected NIH/3T3 cells in medium lacking carbachol. As shown in FIG. 2, under these conditions, cells returned to their nontransformed morphology. In contrast, foci arose when the culture medium was supplemented with carbachol. Furthermore, focus-derived cells were capable of forming large colonies in soft agar, in the presence but not in the absence of agonist (data not shown). Thus, m1 and m3 mACHR transfectants possessed properties of fully malignant cells. These findings demonstrated that m1 and m3 mACHRs were potent transforming agents and that agonist was required for induction and maintenance of malignant transformation.

EXAMPLE 3

Verification of mACHR Expression in NIH/3T3 Transfectants

To directly examine mACHR expression in transfected cells, several m1 and m3 foci were cloned, and evaluated for receptor expression by binding of a labeled nonselective mACHR antagonist, N-methyl-scopolamine ([$^3$H]-NMS). Receptor numbers were found to be higher in cloned m1 and m3 foci as compared to parental geneticin selected mass cultures (TABLE 2). This finding suggested that high levels of receptor expression were required for transforming activity. Binding to m2 and m4 transfected mass cultures was similar to that for m3 transfectants (TABLE 2). Thus, the lack of foci in m2 and m4 transfected cultures demonstrated an intrinsic difference between m1 and m3 as compared to m2 and m4 mACHRs. Binding characteristics were investigated of mACHRs expressed in NIH/3T3 cells. Dissociation constants and total binding sites for representative G418 selected clones, revealed $K_d$ values of 63, 82, 38, and 26 pM for m1–m4 receptors, respectively. These affinities are nearly identical to those which have been previously described in other cell lines (Ashkenazi, et al. (1989) *Nature* 340, 146–150; Buckley, N. J., et al. (1989) *Mol. Pharmacol.* 35, 469–476).

TABLE 2

| Ligand binding to transfected cells. | | |
|---|---|---|
| DNA clone | Binding [$^3$H]NMS (fmoles [$^3$H]NMS/mg protein) Mass Culture | Cloned Focus |
| pDS | <1 | — |
| pDS m1 | 430 | 640 ± 58* |
| pDS m2 | 90 | — |
| pDS m3 | 63 | 496 ± 146* |
| pDS m4 | 40 | — |

The receptor density of each G418 selected mass culture or individual cloned focus was measured by specific binding of the tritiated nonselective mACHR antagonist N-methylscopolamine ([$^3$H]NMS) to membranes prepared from the specified cell lines, as previously described (Jones, S. V. P., et al. (1988) *Mol. Pharmacol.* 34, 421–426). Non-specific binding was determined in the presence of 10 μM atropine. * The data are means ±SEM of 6 cloned foci.

EXAMPLE 4

Quantitation of Transformation Induced by Carbachol

Figure 3:
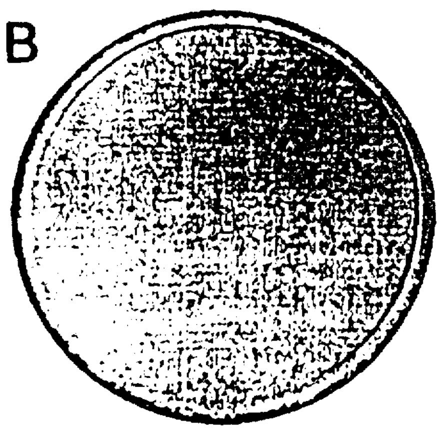
FIG. 3. Ligand dependent transformation of NIH/3T3 cells expressing ml or m3 mAChRs. Approximately 200 cells derived from a clone of NIH/3T3 cells expressing 1100 fmoles of [$^3$H]NMS binding sites/mg protein were plated together with $2\times10^5$ untransfected NIH/3T3 cells. Cultures were grown in the absence of carbachol (A), or in the presence of 0.1 μM (B), 1.0 μM (C), 3.0 μM (D), 10 μM (E) or 100 μM carbachol (F), and stained after 2 weeks.
Figure 3:
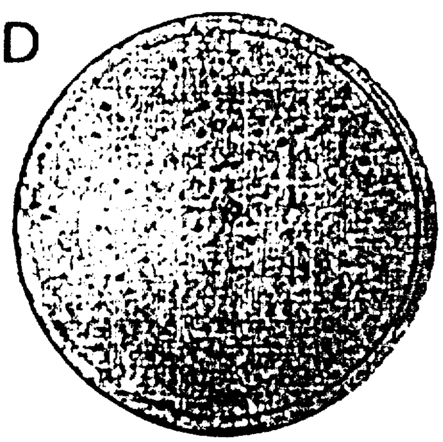
Figure 3:
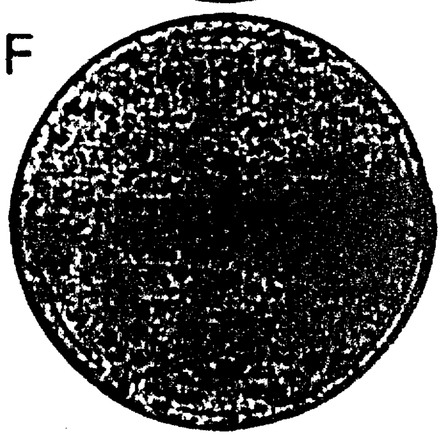

To explore quantitative aspects of transformation induced by activation of m1 and m3 mACHRs, an assay was devised for ligand dependent transformation that involved plating mACHR transfectants on a lawn of NIH/3T3 cells. In absence of carbachol, no foci of transformation were observed. However, when concentrations of the agonist ranging from 100 nM to 1 mM were added to the culture media, foci arose in less than 1 week in a clonal m1 transfectant (FIG. 3). Furthermore, the number of foci observed was directly proportional to ligand concentration (FIG. 3, and see below). At a concentration of 1 mM, 100% of the m1 transfectants plated gave rise to foci of transformation. Under these conditions as well, focus formation was prevented by atropine (10 μm) (data not shown). Taken together, the findings demonstrate that receptor number as well as agonist concentration are direct determinants of transformation in this system.

EXAMPLE 5

Second Messenger Coupling in mACHR Transfectants

Figure 4A:
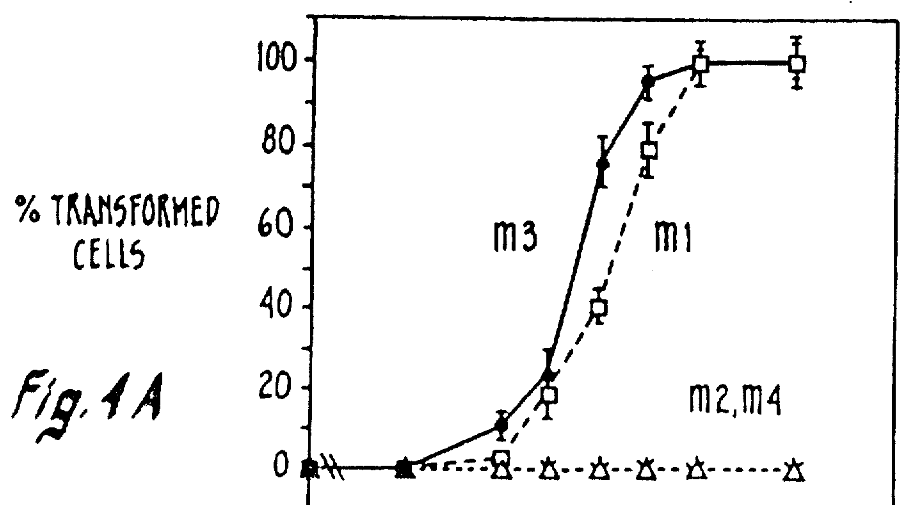
FIG. 4. Effect of carbachol on cell transformation, PI hydrolysis, and cAMP levels in G418 selected NIH/3T3 clones expressing different mACHR subtypes. Carbachol induced cell transformation (A), activation of PI hydrolysis (B), and inhibition of forskolin stimulated cAMP accumulation (C) were measured in cells expressing m1, m2, m3 or m4 mACHRs as indicated. Receptor expression was 600, 300, 370 and 650 fmoles of [$^3$H]NMS binding sites/mg protein for m1–m4 mACHRs, respectively. Cell transformation was determined by plating cells on a lawn of non-transformed NIH/3T3 cells. Cells were maintained in the presence of indicated concentrations of carbachol, and foci were counted 2 weeks later. Each data point represents the average ± SEM of triplicate plates from 2–3 separate experiments, expressed as the ratio of foci to the number of plated cells ×100. PI hydrolysis was determined as described. Each data point represents the average ± SEM for triplicate samples from 3 to 4 separate experiments, expressed as the ratio of [$^3$H]IP accumulated in stimulated versus unstimulated cells. Atropine (10) μM prevented the carbachol-dependent accumulation of ($^3$H]IP (data not shown). Inhibition of adenylyl cyclase was determined by measuring the effect of carbachol on cAMP accumulation induced by forskolin, in the presence of isobutylmethylxanthine (100 μM). Cells, treated for 10 min with saline solution (bar 1) or 1 mM carbachol (bar 2) did not accumulate detectable cAMP. Treatment with 10 mM forskolin alone (bar 3), or in combination with 1 mM carbachol (bar 4) is also shown. cAMP was measured by radioimmunoassay as described. *, $p<0.01$ vs forskolin alone. Data are means ± SEM of three replicate determinations.
Figure 4B:
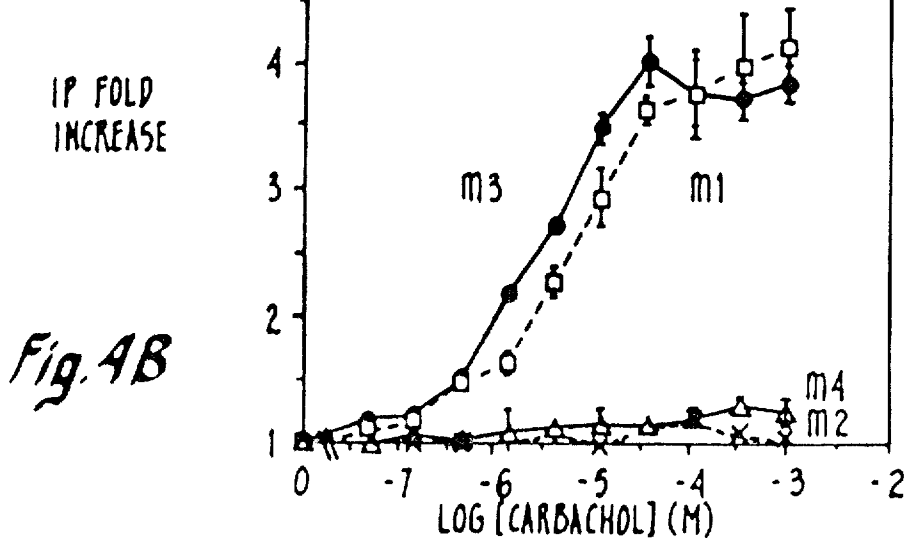
Figure 4C:
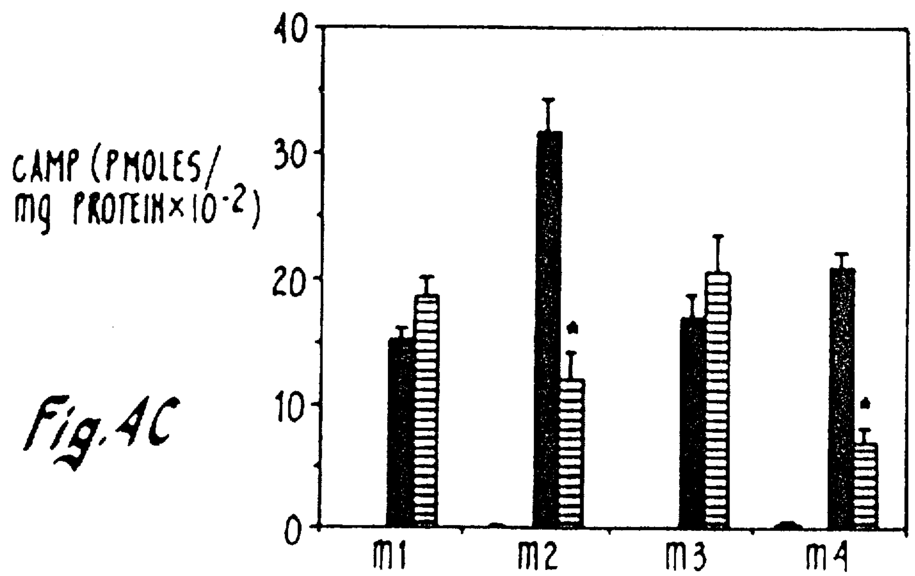

To determine whether mACHRs expressed in NIH/3T3 cells were coupled to second messenger generation systems, transfectants were examined for known biochemical effects in response to agonist. Significant PI hydrolysis was observed in cells expressing m1 or m3 receptors, but not in m2 and m4 expressors even at very high agonist concentration (FIG. 4). Carbachol decreased cAMP levels only in forskolin treated cells expressing m2 and m4 mACHRs (FIG. 4). Similar results were obtained using a number of other clones expressing m2 or m4 mACHRs subtypes (data not shown). These findings demonstrate that known biochemical responses characteristic of mACHRs are reflected in our NIH/3T3 cell transfectants.

EXAMPLE 6

Quantitative Relationship Between Focus Formation and Extent of Phosphatidylinositol Hydrolysis Observations that transformation as well as PI hydrolysis were dose dependent for m1 and m3 transfectants provided an opportunity to characterize the relationship between the biological and biochemical responses to agonist. Thus, G418-selected NIH/3T3 cell clones expressing comparable levels of each mACHR subtype were compared for PI hydrolysis and focus formation in response to varying concentrations of agonist. As shown in FIG. 4, it was observed that curves for PI hydrolysis were nearly superimposable upon those for focus-formation. The half-maximal dose ($EC_{50}$) was then determined for both PI hydrolysis and transformation using several clonal transfectants selected for variations in receptor expression. For each clone examined, the half-maximal concentration of carbachol required for cell transformation was nearly identical to that necessary to stimulate PI hydrolysis (TABLE 3). Furthermore, the maximal PI hydrolysis response was proportional to the number of mACHRs expressed by respective m1 or m3 clonal transfectants.

Very few foci were observed in cells expressing low numbers of m1 or m3 mACHR. In contrast, >95% of m1 or m3 transfectants binding more than 612 or 373 fmoles of [$^3$H]NMS/mg cellular protein, respectively, gave rise to foci of transformation. A similar analysis of the remaining m1 or m3 transfected clones revealed that below a level of 90 to 100 fmoles of [$^3$H]NMS binding per mg protein, no effective agonist-induced focus formation was observed. These findings suggest a low threshold of receptor expression for agonist-induced transformation.

TABLE 3

| Effect of carbachol on PI hydrolysis and transformation | | | | | |
|---|---|---|---|---|---|
| | PI Hydrolysis | | | Transformation | |
| | Maximal activation | | | | |
| Gene | Binding | (fold) | EC50 (μM) | Maximal transportation | $EC_{50}$ (μM) |
| neo | 0 | 1.0 | ND | 0 | ND |
| m1 | 38 | 1.3 | 1 | 2 | * |
| | 612 | 2.2 | 1 | >95 | 10 |
| | 919 | 6.5 | 0.5 | >95 | 6 |
| m2 | 308 | 1.2 | * | 0 | ND |
| m3 | 60 | 1.6 | 3 | 3 | * |
| | 373 | 2.1 | 1 | >95 | 3 |
| | 1309 | 4.1 | 3 | >95 | 8 |
| m4 | 654 | 1.3 | 40 | 0 | ND |

+ fmoles [$^3$H]NMS/mg protein

G418 selected clones expressing different mACHR subtypes were tested for PI hydrolysis and cell transformation in response to carbachol ranging in concentration from 50 nM to 333 μM. Results represent the average from 3–4 experiments. Standard error was less than 5% of the mean for each determination. $EC_{50}$, half maximal concentration. ND, not determined. *, values too low to be determined with sufficient accuracy.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method of identifying reversal of transformation of NIH/3T3 cells, comprising:

(1) introducing a DNA vector contain a gene encoding m1 or m3 type acetyliholine receptor linked to phosphatidylinositol metabolism into NIH/3T3 cells.

(2) culturing said cells on medium containing an agonist of said receptor, (3) determining the amount of agonist-dependent neoplastic transformation;

(4) culturing said cells on medium lacking said agonist; and (5) determining the amount of neoplastic transformation, wherein a decrease in the amount of transformation determined in step (5) compared to that determined in step (3). indicates that the neoplastic transformation caused by said agonist has been reversed.

2. The method according to claim 1 wherein said DNA is a double stranded plasmid containing regions coding for the m1 or m3 acetylcholine receptor gene.

3. The method of claim 2 wherein said plasmid is an expression plasmid.

4. The method according to claim 1 wherein said agonist is an acetylcholine analog.

5. The method according to claim 4 wherein said analog is carbachol.

6. A method for screening a potential transformation inhibiting-agent for its ability to reverse the transformation of an NIH/3T3 cell, comprising:

(1) introducing a DNA vector containing a gene encoding the m1 or m3 type acetylcholine receptor linked to phosphatidylinositol metabolism into an NIH/3T3 cell;

(2) culturing said cell on medium containing an agonist of said receptor and lacking said agent, thereby causing transformation of said cell;

(3) culturing said transformed cell on medium containing an agonist of said receptor and containing said agent; and (4) determining whether said cell remains transformed in the presence of said agent being tested.

7. The method of claim 6, wherein said agent is a competitive inhibitor of said agonist.

8. The method according to claim 6 wherein said DNA is a double stranded plasmid containing regions coding for the m1 or m3 acetylcholine receptor gene.

9. The method according to claim 6 wherein said agonist is an acetylcholine analog.

* * * * *